United States Patent [19]

Konishi et al.

[11] 4,321,081

[45] Mar. 23, 1982

[54] ORTHO-(TRIFLUOROMETHYLSUL-FONAMIDO)BENZAMIDES AS HERBICIDES

[75] Inventors: Hiroyuki Konishi; Shunichi Hashimoto; Hiromichi Oshio, all of Osaka, Japan

[73] Assignee: Sumitomo Chemical Company, Limited, Osaka, Japan

[21] Appl. No.: 250,724

[22] Filed: Apr. 3, 1981

[30] Foreign Application Priority Data

Apr. 11, 1980 [JP] Japan .................................. 55-48252

[51] Int. Cl.$^3$ ...................... A01N 9/16; C07C 143/74
[52] U.S. Cl. .................................... 71/88; 260/239 B; 260/326.47; 260/453 RW; 71/90; 71/94; 71/95; 71/103; 544/58.4; 544/110; 546/226; 546/314; 564/97
[58] Field of Search ................. 564/97; 71/88, 90, 94, 71/95, 103, 76; 544/58.4, 110; 546/226, 314; 260/239 B, 326.47, 453 RW

[56] References Cited

U.S. PATENT DOCUMENTS

| | | | |
|---|---|---|---|
| Re. 29,032 | 11/1976 | Robertson et al. | 564/97 |
| 3,178,339 | 4/1965 | Frick et al. | 564/97 X |
| 3,558,698 | 1/1971 | Harrington et al. | 564/97 |
| 3,629,332 | 12/1971 | Harrington et al. | 564/97 |
| 3,639,474 | 2/1972 | Harrington et al. | 260/556 F |
| 3,920,444 | 11/1975 | Harrington et al. | 71/103 |
| 4,076,519 | 2/1978 | Harrington et al. | 71/103 |
| 4,093,445 | 6/1978 | Arneklev et al. | 71/103 X |
| 4,163,659 | 8/1979 | Harrington et al. | 71/103 X |

FOREIGN PATENT DOCUMENTS

| | | | |
|---|---|---|---|
| 865735 | 4/1961 | United Kingdom | 564/97 |
| 1306564 | 2/1973 | United Kingdom | |

Primary Examiner—Thomas A. Waltz
Attorney, Agent, or Firm—Birch, Stewart, Kolasch & Birch

[57] ABSTRACT

A compound of the formula:

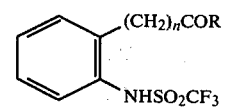

wherein R is $C_1$–$C_4$ alkylamino, $C_3$–$C_4$ alkenylamino, $C_3$–$C_4$ alkynylamino, di($C_1$–$C_4$)alkylamino, di($C_3$–$C_4$)alkenylamino, di($C_3$–$C_4$)alkynylamino, $C_1$–$C_4$ alkyl($C_3$–$C_4$)alkenylamino, $C_1$–$C_4$ alkyl($C_3$–$C_4$)alkynylamino, $C_1$–$C_4$ alkoxyamino, $C_1$–$C_4$ alkyl($C_1$–$C_4$)alkoxyamino, $C_1$–$C_4$ alkylphenylamino, morpholino, thiomorpholino, $C_1$–$C_4$ alkylmorpholino, di($C_1$–$C_4$)alkylmorpholino, pyrrolidino, $C_1$–$C_4$ alkylpyrrolidino, piperidino, $C_1$–$C_4$ alkylpiperidino, hexamethyleneimino or tetrahydropyridino and n is an integer of 0 or 1, or a salt thereof, which is useful as a herbicide.

18 Claims, No Drawings

ORTHO-(TRIFLUOROMETHYLSULFONAMIDO)-BENZAMIDES AS HERBICIDES

The present invention relates to sulfonamide derivatives and their salts, and their production and use.

The acid sulfonamide derivatives are representable by the formula:

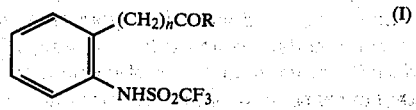

wherein R is $C_1$–$C_4$ alkylamino, $C_3$–$C_4$ alkenylamino, $C_3$–$C_4$ alkynylamino, di($C_1$–$C_4$)alkylamino, di($C_3$–$C_4$)alkenylamino, di($C_3$–$C_4$)alkynylamino, $C_1$–$C_4$ alkyl($C_3$–$C_4$)alkenylamino, $C_1$–$C_4$ alkyl($C_3$–$C_4$)alkynylamino, $C_1$–$C_4$ alkoxyamino, $C_1$–$C_4$ alkyl($C_1$–$C_4$)alkoxyamino, $C_1$–$C_4$ alkylphenylamino, morpholino, thiomorpholino, $C_1$–$C_4$ alkylmorpholino, di($C_1$–$C_4$)alkylmorpholino, pyrrolidino, $C_1$–$C_4$ alkylpyrrolidino, piperidino, $C_1$–$C_4$ alkylpiperidino, hexamethyleneimino or tetrahydropyridino and n is an integer of 0 or 1.

Preferred are the sulfonamide derivatives of the formula (I) wherein R is $C_1$–$C_4$ alkylamino, $C_3$–$C_4$ alkenylamino, $C_3$–$C_4$ alkynylamino, di($C_1$–$C_4$)alkylamino, di($C_3$–$C_4$)alkenylamino, di($C_3$–$C_4$)alkynylamino, $C_1$–$C_4$ alkyl($C_3$–$C_4$)alkenylamino or $C_1$–$C_4$ alkyl($C_3$–$C_4$)alkynylamino and n is an integer of 0. Also preferred are those of the formula (I) wherein R is $C_1$–$C_4$ alkylamino, $C_3$–$C_4$ alkenylamino, $C_3$–$C_4$ alkynylamino, di($C_1$–$C_4$)alkylamino, di($C_3$–$C_4$)alkenylamino, di($C_3$–$C_4$)alkynylamino, $C_1$–$C_4$ alkyl($C_3$–$C_4$)alkenylamino, $C_1$–$C_4$ alkyl($C_3$–$C_4$)alkynylamino, $C_1$–$C_4$ akoxyamino, $C_1$–$C_4$ alkyl ($C_1$–$C_4$)alkoxyamino, $C_1$–$C_4$ alkylphenylamino, morpholino, thiomorpholino, $C_1$–$C_4$ alkylmorpholino, di($C_1$–$C_4$)alkylmorpholino, pyrrolidino, $C_1$–$C_4$ alkylpyrrolidino, piperidino, $C_1$–$C_4$ alkylpiperidino, hexamethyleneimino or tetrahydropyridino and n is an integer of 1.

Particularly preferred are the sulfonamide derivatives of the formula (I) wherein R is $C_1$–$C_4$ alkylamino, allylamino, propargylamino or di($C_2$–$C_3$)alkylamino and n is an integer of 0. Also particularly preferred are those of the formula (I) wherein R is $C_1$–$C_2$ alkylamino, di($C_1$–$C_2$)alkylamino, diallylamino, dipropargylamino, methoxyamino, methoxymethylamino, $C_1$–$C_2$ alkylphenylamino, morpholino, thiomorpholino, pyrrolidino, piperidino, hexamethyleneimino, tetrahydropyridino, methylpiperidino or dimethylpyrrolidino and n is an integer of 1.

In the course of study on various chemical compounds and their herbicidal activity, it has been found that the sulfonamide derivatives (I) have a strong herbicidal activity as well as a high selectivity to crop plants. Thus, the sulfonamide derivatives (I) are highly effective in preventing and exterminating farmland weeds such as Echinochloa utilis, large crabgrass (Digitaria sanguinalis), redroot pigweed (Amaranthus retroflexus), common purslane (Portulaca oleracea) and common lambsquarters (Chenopodium album), smartweeds (Polygonum sp.) and yellow nutsedge (Cyperus esculentus) as well as paddy field weeds such as barnyard grass (Echinochloa crus-galli), pickerel weed (Monochoria vaginalis), false pimpernel (Lindernia pyxidaria) and nutsedge sp. While the prevention and extermination of Cyperus rotundus and Cyperus esculentus in farmland are generally difficult, some of the sulfonamide derivatives (I) of the invention exert a strong herbicidal activity against them. Also, they exhibit a strong herbicidal activity against large seeds such as annual morningglory (Ipomoea purpurea), cocklebur (Xanthium pennsylvanicum), velvetleaf (Abutilon theophrasti), prickly sida (Sida spinosa) and catchweed betstraw (Galium aparine).

Advantageously, the sulfonamide derivatives (I) produce a strong herbicidal potency on the application to farmland, irrespective of soil treatment prior to emergence of weeds and foliar treatment after emergence, without causing any harmful effect on various crop plants (e.g. soybean, cotton, wheat, corn). Still, some of them show a high herbicidal activity and have a wide spectrum on perennial paddy field weeds such as Cyperus serotinus, arrowhead (Sagittaria pygmaea), hardstem bulrush (Scirpus juncoides), slender spikerush (Eleocharis acicularis) and spikerush (Eleocharis kuroguai) in addition to annual paddy field weeds in pre-emergence or post-emergence application without any phytotoxicity to crop plants including rice plants.

Accordingly, the sulfonamide derivatives (I) are useful as herbicides applicable for paddy field and farmland. They are also useful as herbicides to be employed for vegetable garden, orchard, lawn, pasture, tea garden, mulberry field, rubber plantation, forest, non-agricultural land, etc.

British Pat. No. 1,306,564 and U.S. Pat. No. 3,639,474 disclose some trifluoromethanesulfonanilide compounds which have a herbicidal activity. However, there has never been known any trifluoromethanesulfonilide derivative having an N-substituted carbamoyl group, to which the present invention pertains. Further, in comparison with said known compounds, the sulfonamide derivatives (I) exert a much superior herbicidal effect as can be seen from the comparative test results as hereinafter presented.

The sulfonamide derivatives (I) can be produced by the following processes:

(a) A process which comprises reacting an aniline derivative of the formula:

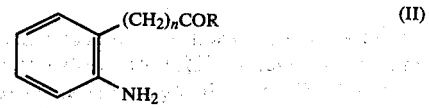

wherein R and n are each as defined above with trifluoromethanesulfonic anhydride or trifluoromethanesulfonyl halide.

The reaction may be carried out by mixing the aniline derivative (II) with trifluoromethanesulfonic anhydride or trifluoromethanesulfonyl halide, if necessary, in the presence of a solvent (e.g. methylene chloride, chloroform, benzene, toluene, xylene, chlorobenzene, dichlorobenzene, dimethoxyethane, dimethylacetamide, dimethylformamide, dimethylsulfoxide). When desired, a dehydrohalogenating agent such as triethylamine, tributylamine, pyridine, N-methylmorphorine, potassium carbonate or sodium carbonate may be present in the reaction system. The reaction temperature may vary from $-15°$ to $50°$ C. and, if the case may be, any below and above temperature than that range may be adopted.

The starting aniline derivative (II) is obtainable, for instance, by the method as disclosed in J.Med.Chem., 13 (1), 144 (1970).

(b) A process which comprises reacting an acid halide derivative of the formula:

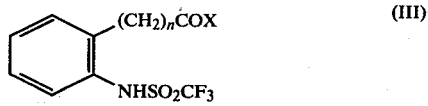

wherein X is halogen (e.g. chlorine, bromine) and n is an integer of 0 or 1 with an amine of the formula:

$$HR \qquad (IV)$$

wherein R is as defined above.

This reaction may be carried out in an appropriate solvent (e.g. tetrahydrofuran, dimethoxyethane, benzene, toluene, xylene, chlorobenzene, dichlorobenzene, methylenechloride, chloroform, dimethylformamide, dimethylsulfoxide). The yield can be increased by using a dehydrohalogenating agent such as triethylamine, tributylamine, pyridine, N-methylmorpholine, potassium carbonate or sodium carbonate, among with triethylamine is the most preferred. The reaction temperature may be from $-15°$ to $50°$ C. but, if the case may be, any below and above temperature than that range may be adopted.

The starting acid halide derivative (III) is novel and can be produced in the following manner:

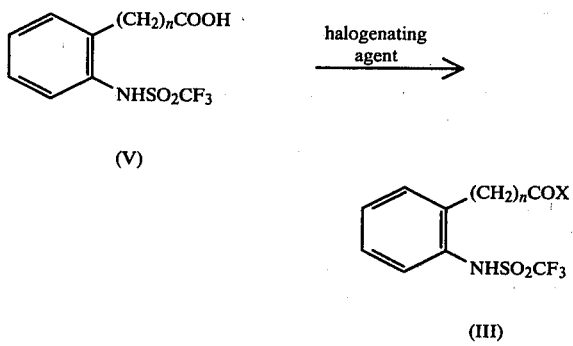

wherein X and n are each as defined above. Namely, the acid halide derivative (III) is obtainable by reacting the compound (V) with a halogenating agent such as thionyl halide (e.g. thionyl chloride, thionyl bromide), phosphorus halide (e.g. phosphorus pentachloride, phosphorus trichloride, phosphorus tribromide) or phosphorus oxyhalide (e.g. phosphoryl trichloride). Among them, thionyl chloride is the most preferred. The reaction may be carried out under heating in the pesence or absence of an appropriate solvent such as ethylene chloride or chloroform.

The compound (V) is obtainable by hydrolyzing the corresponding ester, which may be prepared by the process as disclosed in U.S. Pat. No. 3,639,474.

The sulfonamide derivatives (I) are themselves acidic and can be recovered in the free or salt form depending upon the reaction conditions and the separation procedures. When they are in the salt form, the hydrogen atom attached to the nitrogen atom of the sulfonamide group in the chemical structure of the formula (I) is replaced by any other cation.

The conversion of the sulfonamide derivatives (I) in the free form into the salt form and vice versa can be accomplished by a per se conventional procedure.

Examples of the salts of the sulfonamide derivatives (I) are salts of sodium, potassium, calcium, ammonium, methylammonium, ethylammonium, n-propylammonium, isopropylammonium, n-butylammonium, isobutylammonium, sec-butyl-ammonium, t-butylammonium, n-amylammonium, iso-amylammonium, n-hexylammonium, 2-methylpentylammonium, cyclopentylammonium, cyclohexylammonium, allylammonium, dimethylammonium, diethylammonium, methylethylammonium, di-n-propylammonium, diisopropylammonium, di-n-butylammonium, diisobutylammonium, diallylammonium, trimethylammonium, triethylammonium, tri-n-propylammonium, tri-n-butylammonium, 2-hydroxyethylammonium, methyl-2-hydroxyethylammonium, isopropyl-2-hydroxyethylammonium, dimethyl-2-hydroxyethylammonium, di-2-hydroxyethylammonium, tri-2-hydroxyethylammonium, etc.

These salts are obtainable, for instance, by treating the sulfonamide derivative (I) with an amine in a solvent (e.g. water, tetrahydrofuran, hexane, benzene, toluene, xylene, chlorobenzene, dichlorobenzene, methanol, ethanol, propanol, ethylene glycol, chloroform, dimethoxyethane, dimethylformamide, dimethylsulfoxide), preferably at a temperature of $-15°$ to $50°$ C. to give the corresponding ammonium salt. Further, for instance, said salts are obtainable by treating the sulfonamide derivative (I) with an alkali metal alkoxide (e.g. sodium methoxide, potassium ethoxide) or an inorganic basic compound (e.g. potassium carbonate, sodium carbonate, potassium hydroxide, sodium hydroxide, calcium hydroxide) in a solvent (e.g. water, methanol, ethanol, propanol, ethylene glycol, dimethylformamide, dimethylsulfoxide), preferably at a temperature of $-15°$ to $50°$ C. to give the corresponding alkali metal or alkaline earth metal salt. In the above procedures, the temperature does not indicate the essential range and, depending on the situation, a higher or lower temperature may be adopted.

Practical embodiments of the preparation process of the sulfonamide derivatives (I) as well as the starting acid halide derivatives (III) will be illustratively shown in the following examples.

EXAMPLE 1

To 10 g of N-trifluoromethanesulfonylanthranylic acid, there were dropwise added 27 ml of thionyl chloride under ice-cooling. After completion of the addition, the resultant mixture was heated under reflux until the evolution of the gas stopped. The excessive thionyl chloride was removed from the reaction mixture and the oily residue was distilled under reduced pressure to obtain 8.65 g of o-trifluoromethanesulfonamidobenzoyl chloride. b.p. 93°–97° C./0.7 mmHg. $n_D^{21}$ 1.5168.

EXAMPLE 2

To a solution of 10 g of o-(trifluoromethanesulfonamido)phenylacetic acid in 100 ml of chloroform, there were dropwise added 8.4 g of thionyl chloride. After completion of the addition, the resultant mixture was heated and refluxed until the evolution of the gas stopped. Concentration of the reaction mixture gave a solid substance, which was recrystallized from toluene to give 7.6 g of o-(trifluoromethanesulfonamido)phenylacetyl chloride. M.P. 94°–95° C.

EXAMPLE 3

N-t-Butyl-2-aminobenzamide (2 g) and triethylamine (1.05 g) were dissolved in chloroform (50 ml), and while maintaining at 0°–5° C., trifluoromethanesulfonic anhydride (2.93 g) was dropwise added thereto. The resultant mixture was refluxed for 2 hours. The chloroform layer was washed with a 5% aqueous hydrochloric acid solution (50 ml) and water (50 ml) in order and concentrated to give an oily substance, which was solidified on cooling.

The oily substance was then taken into a 10% aqueous sodium hydroxide solution (80 ml) and stirred. Insoluble materials were removed by chloroform, and the alkaline solution was made acidic by hydrochloric acid, whereby an oily substance was precipitated and, on cooling solidified. The solid substance was collected and recrystallized from a mixture of ethanol and water to give 1.6 g of N-t-butyl-2-(trifluoromethanesulfonamido)benzamide. M.P. 108.5°–110.5° C.

EXAMPLE 4

Into a 500 ml four-necked flask, there was charged tetrahydrofuran (200 ml) containing ethylamine (10 g), and while maintaining at 0°–5° C., a solution of N-trifluoromethanesulfonylanthranylic acid chloride (30 g) in tetrahydrofuran (100 ml) was dropwise added thereto. After completion of the addition, the reaction mixture was allowed to stand at room temperature for 2 hours. Removal of the salt and concentration of the mother liquor gave an oily substance, which was solidified on cooling. The solid substance was recrystallized from a mixture of ethanol and water to give 25 g of N-ethyl-2-(trifluoromethanesulfonamido)benzamide. M.P. 85.5°–87° C.

EXAMPLE 5

To tetrahydrofuran (20 ml) containing diethylamine (0.2 g) was added N-methyl-2-(trifluoromethanesulfonamido)benzamide (0.8 g), and the resultant mixture was stirred for about 5 minutes. Removal of tetrahydrofuran by distillation gave 0.75 g of the diethylammonium salt of N-methyl-2-(trifluoromethanesulfonamido)benzamide. M.P. 76.5°–78.5° C.

EXAMPLE 6

Sodium hydroxide (0.1 g) was dissolved in ethanol (20 ml), and N-methyl-2-(trifluoromethanesulfonamido)benzamide (0.8 g) was added thereto. After allowed to stand for a while, ethanol was removed by distillation to give 0.8 g of the sodium salt of N-methyl-2-(trifluoromethanesulfonamido)benzamide.

EXAMPLE 7

Into a 100 ml flask, there was charged tetrahydrofuran (20 ml) containing dimethylamine (0.3 g), and while maintaining at 5° C., a solution of o-(trifluoromethanesulfonamido)phenylacetyl chloride (1 g) in tetrahydrofuran (5 ml) was dropwise added thereto with stirring. After completion of the addition, the reaction mixture was allowed to stand at room temperature for 2 hours. The reaction mixture was concentrated to give the residue, a 5% aqueous hydrochloric acid solution was added thereto, and the resultant mixture was extracted with toluene. The extracted toluene was concentrated to give an oily substance, which was solidified by allowing it to stand. The solid substance was recrystallized from a mixture of ethanol and water to give 0.6 g of N,N-dimethyl-(o-trifluoromethanesulfonamido)phenylacetamide. M.P. 75°–76° C.

EXAMPLE 8 o-Aminophenylacetylmorpholine (9.8 g) and triethylamine (4.5 g) were dissolved in chloroform (200 ml), and while maintaining at 0°–5° C., trifluoromethanesulfonic acid anhydride (12.55 g) was dropwise added thereto. After completion of the addition, the reaction mixture was allowed to stand under reflux for 2 hours. The chloroform layer was washed with a 5% aqueous hydrochloric acid solution (100 ml) and water (100 ml) in order and concentrated to give an oily substance, which was solidified by allowing it to stand. The solid substance was recrystallized from a mixture of ethanol and water to give 8.14 g of N-[o-(trifluoromethanesulfonamido)phenylacetyl]morpholine. M.P. 95.5°–97° C.

In the same manner as above, there are produced other sulfonamide derivatives (I), of which some specific examples are shown in Table 1 below:

TABLE 1

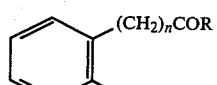

| Compound No. | Chemical structure | | Physical constant | Elementary analysis (%) | | | | |
|---|---|---|---|---|---|---|---|---|
| | n | R | | | | C | H | N | S |
| 1 | 0 | —NHCH$_3$ | M.P. 92–94.5° C. | Calcd. Found | 38.30 38.12 | 3.21 3.20 | 9.93 9.83 | 11.36 11.15 |
| 2 | 0 | —NHC$_2$H$_5$ | M.P. 85.5–87° C. | Calcd. Found | 40.54 40.39 | 3.74 3.72 | 9.46 9.44 | 10.82 10.84 |
| 3 | 0 | —NHC$_3$H$_7$(n) | M.P. 54–55.5° C. | Calcd. Found | 42.58 42.71 | 4.22 4.40 | 9.03 9.13 | 10.33 10.48 |
| 4 | 0 | —NHC$_3$H$_7$(iso) | M.P. 96–97.5° C. | Calcd. Found | 42.58 42.40 | 4.22 4.27 | 9.03 8.92 | 10.33 10.18 |
| 5 | 0 | —NHCH$_2$CH=CH$_2$ | M.P. 42–44° C. | Calcd. Found | 42.86 43.11 | 3.60 3.57 | 9.09 9.01 | 10.40 10.45 |
| 6 | 0 | —NHCH$_2$C≡CH | M.P. 75.5–78° C. | Calcd. Found | 43.14 43.20 | 2.96 2.91 | 9.15 9.15 | 10.47 10.63 |
| 7 | 0 | —NHC$_4$H$_9$(t) | M.P. 108.5–110.5° C. | Calcd. Found | 44.44 44.38 | 4.66 4.59 | 8.64 8.66 | 9.89 9.97 |
| 8 | 0 | —N(C$_2$H$_5$)$_2$ | M.P. 118.5–119.5° C. | Calcd. Found | 44.44 44.35 | 4.66 4.83 | 8.64 8.63 | 9.89 10.08 |

TABLE 1-continued $$\text{(structure with (CH}_2)_n\text{COR and NHSO}_2\text{CF}_3\text{ on benzene ring)}$$

| Compound No. | n | R | Physical constant | | Elementary analysis (%) | | | |
|---|---|---|---|---|---|---|---|---|
| | | | | | C | H | N | S |
| 9 | 0 | −N(C₃H₇(n))(C₃H₇(n)) | M.P. 134–136° C. | Calcd. | 47.72 | 5.43 | 7.95 | 9.10 |
| | | | | Found | 47.58 | 5.42 | 7.71 | 9.09 |
| 10 | 0 | —NHCH₃ (diethylamine salt) | M.P. 76.5–78.5° C. | Calcd. | 43.94 | 5.67 | 11.82 | 9.02 |
| | | | | Found | 44.21 | 5.87 | 11.68 | 8.86 |
| 11 | 0 | —NHC₂H₅ (diethylamine salt) | M.P. 84–89° C. | Calcd. | 45.52 | 6.00 | 11.37 | 8.68 |
| | | | | Found | 45.51 | 5.93 | 11.31 | 8.84 |
| 12 | 0 | —NHCH₃ (triethylamine salt) | M.P. 98.5–102° C. | Calcd. | 46.99 | 6.31 | 10.96 | 8.36 |
| | | | | Found | 47.11 | 6.26 | 11.13 | 8.18 |
| 13 | 0 | —NHCH₃ (n-propylamine salt) | $n_D^{17.5}$ 1.5108 | Calcd. | 42.22 | 5.32 | 12.31 | 9.39 |
| | | | | Found | 42.28 | 5.25 | 12.24 | 9.17 |
| 14 | 0 | —NHCH₃ (ethanolamine salt) | $n_D^{17.5}$ 1.5248 | Calcd. | 38.49 | 4.70 | 12.24 | 9.34 |
| | | | | Found | 38.55 | 4.69 | 12.26 | 9.18 |
| 15 | 0 | —NHCH₃ (potassium salt) | Amorphous | Calcd. | 33.75 | 2.52 | 8.74 | 10.01 |
| | | | | Found | 33.51 | 2.39 | 8.46 | 9.75 |
| 16 | 0 | —NHCH₃ (sodium salt) | Amorphous | Calcd. | 35.53 | 2.65 | 9.21 | 10.54 |
| | | | | Found | 35.36 | 2.50 | 9.04 | 10.48 |
| 17 | 1 | —NHCH₃ | M.P. 102.5–104° C. | Calcd. | 40.54 | 3.74 | 9.46 | 10.82 |
| | | | | Found | 40.70 | 3.73 | 9.28 | 10.59 |
| 18 | 1 | —NHC₂H₅ | M.P. 123–124° C. | Calcd. | 42.58 | 4.22 | 9.03 | 10.33 |
| | | | | Found | 42.40 | 4.20 | 8.91 | 10.18 |
| 19 | 1 | —NHOCH₃ | $n_D^{26.5}$ 1.4868 | Calcd. | 38.47 | 3.55 | 8.97 | 10.27 |
| | | | | Found | 38.67 | 3.50 | 8.98 | 10.65 |
| 20 | 1 | −N(CH₃)(CH₃) | M.P. 75–76° C. | Calcd. | 42.58 | 4.22 | 9.03 | 10.33 |
| | | | | Found | 42.43 | 4.15 | 9.19 | 10.30 |
| 21 | 1 | −N(C₂H₅)(C₂H₅) | M.P. 69.5–70.5° C. | Calcd. | 46.15 | 5.06 | 8.28 | 9.48 |
| | | | | Found | 46.23 | 5.05 | 8.22 | 9.43 |
| 22 | 1 | −N(C₃H₇(n))(C₃H₇(n)) | $n_D^{26.5}$ 1.4880 | Calcd. | 49.17 | 5.78 | 7.65 | 8.75 |
| | | | | Found | 49.28 | 5.46 | 7.64 | 8.71 |
| 23 | 1 | −N(CH₂CH=CH₂)(CH₂CH=CH₂) | $n_D^{26.5}$ 1.5052 | Calcd. | 49.72 | 4.73 | 7.73 | 8.85 |
| | | | | Found | 49.82 | 4.74 | 7.71 | 9.03 |
| 24 | 1 | −N(CH₂C≡CH)(CH₂C≡CH) | $n_D^{24}$ 1.5125 | Calcd. | 50.28 | 3.66 | 7.82 | 8.95 |
| | | | | Found | 50.02 | 3.84 | 7.65 | 9.09 |
| 25 | 1 | −N(CH₃)(C₃H₇(n)) | $n_D^{22.5}$ 1.4960 | Calcd. | 46.15 | 5.06 | 8.28 | 9.48 |
| | | | | Found | 46.15 | 5.10 | 8.35 | 9.28 |
| 26 | 1 | −N(C₂H₅)(C₃H₇(iso)) | $n_D^{21}$ 1.4935 | Calcd. | 47.72 | 5.43 | 7.95 | 9.10 |
| | | | | Found | 47.85 | 5.45 | 7.97 | 9.19 |
| 27 | 1 | −N(C₂H₅)(C₃H₇(n)) | $n_D^{21}$ 1.4940 | Calcd. | 47.72 | 5.43 | 7.95 | 9.10 |
| | | | | Found | 47.63 | 5.49 | 7.85 | 9.23 |
| 28 | 1 | −N(CH₃)(OCH₃) | $n_D^{26.5}$ 1.5041 | Calcd. | 40.49 | 4.02 | 8.59 | 9.83 |
| | | | | Found | 40.71 | 3.93 | 8.57 | 9.60 |
| 29 | 1 | −N(CH₃)(C₆H₅) | M.P. 98.5–99° C. | Calcd. | 51.61 | 4.06 | 7.52 | 8.61 |
| | | | | Found | 51.43 | 4.00 | 7.35 | 8.88 |

TABLE 1-continued

![structure: benzene ring with (CH2)nCOR and NHSO2CF3 substituents]

| Compound No. | Chemical structure n | R | Physical constant | | Elementary analysis (%) C | H | N | S |
|---|---|---|---|---|---|---|---|---|
| 30 | 1 | —N(C2H5)(C6H5) | M.P. 95–96° C. | Calcd. Found | 52.84 52.67 | 4.43 4.56 | 7.25 7.33 | 8.30 8.12 |
| 31 | 1 | morpholino | M.P. 95.5–97° C. | Calcd. Found | 44.32 44.29 | 4.29 4.32 | 7.95 7.89 | 9.10 9.06 |
| 32 | 1 | pyrrolidino | $n_D^{25}$ 1.5075 | Calcd. Found | 46.43 46.15 | 4.50 4.44 | 8.33 8.21 | 9.53 9.54 |
| 33 | 1 | piperidino | $n_D^{25}$ 1.5095 | Calcd. Found | 48.00 47.81 | 4.89 4.84 | 8.00 7.93 | 9.15 9.22 |
| 34 | 1 | hexamethyleneimino | M.P. 54–55° C. | Calcd. Found | 49.44 49.18 | 5.26 5.27 | 7.69 7.59 | 8.80 9.00 |
| 35 | 1 | 1,2,3,6-tetrahydropyridino | M.P. 90–91° C. | Calcd. Found | 48.27 48.22 | 4.34 4.34 | 8.04 8.07 | 9.20 9.36 |
| 36 | 1 | 2-methylpiperidino | $n_D^{28}$ 1.5026 | Calcd. Found | 49.44 49.49 | 5.26 5.31 | 7.69 7.69 | 8.80 8.89 |
| 37 | 1 | 2,5-dimethylpyrrolidino | $n_D^{26}$ 1.5040 | Calcd. Found | 49.44 49.50 | 5.26 5.42 | 7.69 7.77 | 8.80 9.07 |
| 38 | 1 | 4-methylpiperidino | $n_D^{25.5}$ 1.5043 | Calcd. Found | 49.44 49.41 | 5.26 5.35 | 7.69 7.82 | 8.80 8.68 |
| 39 | 1 | thiomorpholino | M.P. 157.5–158° C. | Calcd. Found | 42.62 42.35 | 4.13 4.20 | 7.65 7.71 | 16.96 17.23 |
| 40 | 1 | 2,6-dimethylmorpholino | M.P. 88–89° C. | Calcd. Found | 47.37 47.15 | 5.03 5.09 | 7.36 7.28 | 8.43 8.75 |

In the practical usage of the sulfonamide derivatives (I), they may be applied as such or in any preparation form such as granules, fine granules, dusts, coarse dusts, wettable powders, emulsifiable concentrates, aqueous solutions or oily suspensions.

For production of said preparation forms, solid or liquid carriers or diluents may be used. As for the solid carrier or diluent, there may be exemplified mineral powders (e.g. kaolin, bentonite, clay, montmorillonite, talc, diatomaceous earth, mica, vermiculite, gypsum, calcium carbonate, apatite), vegetable powders (e.g. soybean powder, flour, wooden powder, tobacco powder, starch, crystalline cellulose), high molecular weight compounds (e.g. petroleum resin, polyvinyl chloride, dammar gum, ketone resin), alumina, wax and the like. As for the liquid carrier or diluent, there may be exemplified alcohols (e.g. methanol), aromatic hydrocarbons (e.g. toluene, benzene, xylene, methylnaphthalene), halogenated hydrocarbons (e.g. chloroform, carbon tetrachloride, monochlorobenzene), ethers (e.g. dioxane, tetrahydrofuran), ketones (e.g. acetone, methylethylketone, cyclohexanone), esters (e.g. ethyl acetate, butyl acetate, ethylene glycol acetate), acid amides (e.g. dimethylformamide), nitriles (e.g. acetonitrile), ether alcohols (e.g. ethylene glycol ethyl ether), water and the like.

A surface active agent used for emulsification, dispersion or spreading may be any of the non-ionic, anionic, cationic and amphoteric type of agents. Examples of the surface active agent include polyoxyethylene alkyl ethers, polyoxyethylene alkylaryl ethers, polyoxyethylene fatty acid esters, sorbitan fatty acid esters, polyoxyethylene sorbitan fatty acid esters, oxyethylene-oxypropylene polymers, polyoxyethylene alkyl phosphates, fatty acid salts, alkyl sulfates, alkyl sulfonates, alkylaryl sulfonates, alkyl phosphates, polyoxyethylene alkyl sulfates, quaternary ammonium salts and the like. But, the surface active agent is not of course limited to these compounds. If necessary, gelatin, casein, sodium alginate, starch, agar, polyvinyl alcohol or the like may be used as an auxiliary agent.

In the herbicidal composition of this invention, the content of the sulfonamide derivatives (I) may be usually from 1 to 95% by weight, preferably from 3 to 80% by weight.

Practical embodiments of the herbicidal composition according to the invention are illustratively shown in the following examples wherein part(s) and % are by weight.

Preparation Example 1

Eighty parts of Compound No. 4, 3 parts of alkylsulfate, 2 parts of ligninsulfonate and 15 parts of white carbon are well mixed while being powdered to obtain a wettable powder preparation.

Preparation Example 2

Eighty parts of Compound No. 31, 6 parts of 50% powder of polyoxyethylene alkylaryl ether, 2 parts of ligninsulfonate and 12 parts of white carbon are well mixed while being powdered to obtain a wettable powder preparation.

Preparation Example 3

Twenty parts of Compound No. 2, 10 parts of an emulsifier ("Sorpol SM-100" manufactured by Toho Chemical Co., Ltd.), 50 parts of cyclohexanone and 20 parts of xylene are well mixed to obtain an emulsifiable concentrate preparation.

Preparation Example 4

Five parts of Compound No. 37, 1 part of white carbon, 35 parts of bentonite and 59 parts of clay are well mixed while being powdered. The mixture is then kneaded with water, granulated and dried to obtain a granule preparation.

Preparation Example 5

Three parts of Compound No. 32, 0.3 part of isopropyl phosphate, 66.7 parts of clay and 30 parts of talc are well mixed while being powdered to obtain a dust preparation.

Preparation Example 6

Ten parts of Compound No. 11, 5 parts of polyoxyethylene alkylaryl ether and 1 part of ligninsulfonate are dissolved in 84 parts of water to obtain an aqueous solution preparation.

The sulfonamide derivatives (I) may be used together with other herbicides to improve their activity as herbicides, and in some cases, to produce a synergistic effect. As the herbicides to be mixed with, there may be given phenoxy series herbicides such as 2,4-dichlorophenoxyacetic acid, 2-methyl-4-chlorophenoxybutyric acid and 2-methyl-4-chlorophenoxyacetic acid (including esters and salts thereof); diphenyl ether series herbicides such as 2,4-dichlorophenyl-4'-nitrophenyl ether, 2,4,6-trichlorophenyl-4'-nitrophenyl ether, 2-chloro-4-trifluoromethylphenyl-3'-ethoxy-4'-nitrophenyl ether, 2,4-dichlorophenyl-4'-nitro-3'-methoxyphenyl ether and 2,4-dichlorophenyl-3'-methoxycarbonyl-4'-nitrophenyl ether; triazine series herbicides such as 2-chloro-4,6-bisethylamino-1,3,5-triazine, 2-chloro-4-ethylamino-6-isopropylamino-1,3,5-triazine, 2-methylthio-4,6-bisethylamino-1,3,5-triazine, 2-methylthio-4,6-bisisopropylamino-1,3,5-triazine and 4-amino-6-t-butyl-3-methylthio-1,2,4-triazin-5-one; urea series herbicides such as 3-(3,4-dichlorophenyl)-1,1-dimethylurea, 3-(3,4-dichlorophenyl)-1-methoxy-1-methylurea and 1-(2,2-dimethylbenzyl)-3-p-tolylurea; carbamate series herbicides such as isopropyl-N-(3-chlorophenyl)carbamate and methyl-N-(3,4-dichlorophenyl)carbamate; thiolcarbamate series herbicides such as S-(4-chlorobenzyl)-N,N-diethylthiolcarbamate, S-ethyl-N,N-hexamethylenethiolcarbamate, S-ethyl-N,N'-diisobutylthiolcarbamate, and S-ethyl-N,N-di-n-propylthiolcarbamate and S-n-propyl-N,N-din-propylthiolcarbamate; acid anilide series herbicides such as 3,4-dichloropropionanilide, N-methoxymethyl-2,6-diethyl-α-chloroacetanilide, 2-chloro-2',6'-diethyl-N-butoxymethylacetanilide, 2-chloro-2',6'-diethyl-N-(n-propoxyethyl)acetanilide, N-chloroacetyl-N-(2,6-diethylphenyl)glycine ethyl ester and 2-chloro-N-(2-ethyl-6-methylphenyl)acetamide; uracil series herbicides such as 5-bromo-3-sec-butyl-6-methyluracil and 3-cyclohexyl-5,6-trimethyleneuracil; pyridinium chloride series herbicides such as 1,1'-dimethyl-4,4-bispyridinium chloride; phosphorus series herbicides such as N,N-bis(phosphonomethyl)glycine, O-ethyl-O-(2-nitro-5-methylphenyl)-N-sec-butylphosphoroamidothioate, S-(2-methyl-1-piperidylcarbonylmethyl) O,O-di-n-propyldithiophosphate and S-(2-methyl-1-piperidylcarbonylmethyl) O,O-diphenyldithiophosphate; toluidine series herbicides such as α,α,α-trifluoro-2,6-dinitro-N,N-dipropyl-p-toluidine and 2,6-dinitro-N-sec-butyl-3,4-xylidine; 5-tert-butyl-3-(2,4-dichloro-5-isopropoxyphenyl)-1,3,4-oxadiazolin-2-one; 3-isopropyl-1H-2,1,3-benzothiadiazin(4)-3H-one-2,2-dioxide; α-(β-naphthoxy)propionanilide; 4-(2,4-dichlorobenzoyl)-1,3-dimethylpyrazol-5-yl-p-toluenesulfonate; 4'-phenylsulfonyl-1,1,1,-trifluorosulfono-O-toluidide; 4-chloro-5-methylamino-2-(3-trifluoromethylphenyl)pyridazon-3(2H)-one and the like. But, the herbicides are not limited to these examples.

The herbicides of the invention may be applied together with insecticides, nematocides, fungicides, plant growth regulators, fertilizers, etc.

When the sulfonamide derivative (I) is used as a herbicide, it may be applied before or after germination of weeds in an amount within a wide range. The amount may be usually from about 10 grams to 1 kilogram per 10 ares, preferably from about 50 grams to 600 grams per 10 ares.

Some test examples which show the herbicidal activity of the sulfonamide derivatives (I) are shown in the following Examples wherein % is by weight.

EXAMPLE I

Seeds of large crabgrass, redroot pigweed, annual morningglory and velvetleaf, tubers of *Cyperus esculentus* and seeds of soybean, cotton and wheat were sowed or planted in a plastic tray (20 cm (width)×30 cm (length)) and covered with soil. A required amount of the test compound each formulated into an emulsifiable concentrate preparation and diluted with water was applied to the soil by means of a hand sprayer. Cultivation was carried out in a greenhouse, and the herbicidal activity and phytotoxicity of the test compound were checked 20 days after the application. The results are shown in Table 2. The herbicidal activity was evaluated in figures ranging from 0 to 5. The phytotoxicity to the crop plants was also indicated on the same standard as that of the herbicidal activity.

| Figures | Percentage of growth inhibition (%) |
|---------|-------------------------------------|
| 0       | 0–9                                 |
| 1       | 10–29                               |
| 2       | 30–49                               |
| 3       | 50–69                               |
| 4       | 70–89                               |
| 5       | 90–100                              |

TABLE 2

| Compound No. | Dosage of active ingredient (g/are) | Herbicidal activity | | | | | Phytotoxicity | | |
|---|---|---|---|---|---|---|---|---|---|
| | | Large crabgrass | Redroot pigweed | Annual morningglory | Velvet-leaf | Cyperus esculentus | Soybean | Cotton | Wheat |
| 1  | 40 | 5 | 5 | 5 | 5 | 5 | 0 | 1 | 1 |
|    | 20 | 5 | 5 | 4 | 5 | 5 | 0 | 0 | 0 |
| 2  | 40 | 5 | 5 | 5 | 5 | 5 | 0 | 0 | 0 |
|    | 20 | 4 | 5 | 5 | 4 | 5 | 0 | 0 | 0 |
| 3  | 40 | 4 | 5 | 5 | 4 | 5 | 0 | 0 | 0 |
|    | 20 | 4 | 5 | 5 | 4 | 5 | 0 | 0 | 0 |
| 4  | 40 | 5 | 5 | 5 | 5 | 5 | 0 | 0 | 0 |
|    | 20 | 4 | 5 | 5 | 4 | 5 | 0 | 0 | 0 |
| 5  | 40 | 4 | 5 | 5 | 4 | 5 | 0 | 0 | 0 |
|    | 20 | 4 | 4 | 4 | 3 | 5 | 0 | 0 | 0 |
| 6  | 40 | 4 | 5 | 5 | 4 | 5 | 0 | 0 | 0 |
|    | 20 | 4 | 5 | 5 | 4 | 5 | 0 | 0 | 0 |
| 7  | 40 | 4 | 5 | 5 | 3 | 5 | 0 | 0 | 0 |
|    | 20 | 4 | 4 | 4 | 3 | 5 | 0 | 0 | 0 |
| 8  | 40 | 5 | 5 | 5 | 5 | 5 | 0 | 0 | 0 |
|    | 20 | 3 | 5 | 5 | 4 | 5 | 0 | 0 | 0 |
| 9  | 40 | 4 | 5 | 4 | 3 | 5 | 0 | 0 | 0 |
|    | 20 | 4 | 5 | 4 | 2 | 5 | 0 | 0 | 0 |
| 10 | 40 | 5 | 5 | 5 | 4 | 5 | 0 | 0 | 0 |
|    | 20 | 5 | 5 | 5 | 4 | 5 | 0 | 0 | 0 |
| 11 | 40 | 5 | 5 | 5 | 5 | 5 | 0 | 0 | 0 |
|    | 20 | 4 | 5 | 5 | 4 | 5 | 0 | 0 | 0 |
| 12 | 40 | 5 | 5 | 5 | 5 | 5 | 0 | 0 | 0 |
|    | 20 | 5 | 5 | 5 | 4 | 5 | 0 | 0 | 0 |
| 13 | 40 | 5 | 5 | 5 | 5 | 5 | 0 | 0 | 0 |
|    | 20 | 5 | 5 | 5 | 4 | 5 | 0 | 0 | 0 |
| 14 | 40 | 5 | 5 | 5 | 5 | 5 | 0 | 0 | 0 |
|    | 20 | 5 | 5 | 5 | 4 | 5 | 0 | 0 | 0 |
| 15 | 40 | 5 | 5 | 5 | 5 | 5 | 0 | 0 | 0 |
|    | 20 | 5 | 5 | 5 | 4 | 5 | 0 | 0 | 0 |
| 16 | 40 | 5 | 5 | 5 | 5 | 5 | 0 | 0 | 0 |
|    | 20 | 5 | 5 | 5 | 4 | 5 | 0 | 0 | 0 |
| 17 | 40 | 5 | 5 | 5 | 5 | 5 | 0 | 0 | — |
|    | 20 | 4 | 5 | 5 | 5 | 5 | 0 | 0 | — |
| 18 | 40 | 4 | 5 | 5 | 5 | 5 | 0 | 0 | — |
|    | 20 | 4 | 5 | 5 | 5 | 4 | 0 | 0 | — |
| 19 | 40 | 4 | 5 | 5 | 4 | 5 | 0 | 0 | — |
|    | 20 | 4 | 5 | 4 | 4 | 4 | 0 | 0 | — |
| 20 | 40 | 5 | 5 | 5 | 5 | 5 | 0 | 0 | — |
|    | 20 | 5 | 5 | 5 | 5 | 5 | 0 | 0 | — |
| 21 | 40 | 5 | 5 | 5 | 5 | 5 | 0 | 0 | — |
|    | 20 | 5 | 5 | 5 | 5 | 5 | 0 | 0 | — |
| 22 | 80 | 4 | 5 | 4 | 4 | 5 | 0 | 0 | — |
|    | 40 | 3 | 5 | 3 | 4 | 4 | 0 | 0 | — |
| 23 | 80 | 5 | 5 | 4 | 4 | 5 | 1 | 1 | — |
|    | 40 | 5 | 5 | 4 | 3 | 5 | 1 | 0 | — |
| 24 | 40 | 5 | 5 | 5 | 5 | 5 | 1 | 0 | — |
|    | 20 | 5 | 5 | 5 | 4 | 5 | 0 | 0 | — |
| 25 | 40 | 5 | 5 | 5 | 5 | 5 | 0 | 0 | — |
|    | 20 | 5 | 5 | 5 | 5 | 5 | 0 | 0 | — |
| 26 | 40 | 5 | 5 | 5 | 4 | 5 | 1 | 0 | — |
|    | 20 | 5 | 5 | 4 | 4 | 5 | 0 | 0 | — |
| 27 | 40 | 5 | 5 | 4 | 4 | 5 | 1 | 0 | — |
|    | 20 | 5 | 5 | 4 | 4 | 5 | 0 | 0 | — |
| 28 | 40 | 5 | 5 | 5 | 5 | 5 | 1 | 0 | — |
|    | 20 | 5 | 5 | 5 | 5 | 5 | 0 | 0 | — |
| 29 | 80 | 5 | 5 | 4 | 4 | 5 | 0 | 0 | — |
|    | 40 | 4 | 5 | 4 | 3 | 5 | 0 | 0 | — |
| 30 | 80 | 4 | 5 | 5 | 5 | 5 | 0 | 0 | — |
|    | 40 | 4 | 5 | 5 | 5 | 5 | 0 | 0 | — |
| 31 | 40 | 5 | 5 | 5 | 5 | 5 | 1 | 1 | — |
|    | 20 | 5 | 5 | 5 | 5 | 5 | 0 | 0 | — |
| 32 | 80 | 5 | 5 | 5 | 5 | 5 | 0 | 0 | — |

TABLE 2-continued

| Compound No. | Dosage of active ingredient (g/are) | Herbicidal activity | | | | | Phytotoxicity | | |
|---|---|---|---|---|---|---|---|---|---|
| | | Large crabgrass | Redroot pigweed | Annual morningglory | Velvet-leaf | *Cyperus esculentus* | Soybean | Cotton | Wheat |
| 33 | 40 | 4 | 5 | 5 | 5 | 5 | 0 | 0 | — |
| | 80 | 5 | 5 | 5 | 5 | 5 | 0 | 1 | — |
| 34 | 40 | 4 | 5 | 5 | 4 | 5 | 0 | 0 | — |
| | 80 | 5 | 5 | 5 | 4 | 5 | 0 | 0 | — |
| 35 | 40 | 5 | 5 | 4 | 4 | 5 | 0 | 0 | — |
| | 80 | 5 | 5 | 5 | 5 | 5 | 0 | 1 | — |
| 36 | 40 | 5 | 5 | 5 | 4 | 5 | 0 | 0 | — |
| | 80 | 5 | 5 | 5 | 5 | 5 | 1 | 1 | — |
| 37 | 40 | 5 | 5 | 5 | 4 | 5 | 0 | 0 | — |
| | 80 | 5 | 5 | 5 | 4 | 5 | 1 | 0 | — |
| 38 | 40 | 5 | 5 | 5 | 4 | 5 | 0 | 0 | — |
| | 20 | 4 | 5 | 4 | 4 | 5 | 1 | 0 | — |
| 39 | 40 | 4 | 5 | 5 | 5 | 5 | 0 | 0 | — |
| | 20 | 3 | 5 | 5 | 5 | 5 | 0 | 1 | — |
| Control* A | 40 | 4 | 4 | 1 | 2 | 4 | 2 | 2 | 2 |
| | 20 | 4 | 2 | 0 | 1 | 2 | 1 | 0 | 1 |
| Control** B | 40 | 3 | 4 | 3 | 3 | 3 | 3 | 2 | 1 |
| | 20 | 3 | 2 | 2 | 2 | 1 | 2 | 1 | 1 |

Note:

*Compound disclosed in British patent 1,306,564 (known as "Perfluidone"): 
$\text{C}_6\text{H}_5-\text{SO}_2-\text{C}_6\text{H}_3(\text{CH}_3)-\text{NHSO}_2\text{CF}_3$

**Compound disclosed in U.S. Pat. No. 3,639,474: 
$\text{C}_6\text{H}_4(\text{CONH}_2)-\text{NHSO}_2\text{CF}_3$

EXAMPLE II

A Wagner's pot of 14 cm in diameter was filled with 1.5 kg of paddy field soil and flooded with water to make a paddy field condition. Rice seedlings of 3-leaf growth stage were transplanted in the pot, and seeds of pickerel weed and *Scirpus Hotarui*, and buds of slender spikerush, which tided over the winter, were further sowed or planted therein. A required amount of the test compound was applied to the soil under a flooded condition. Twenty-five days thereafter, the herbicidal activity and phytotoxicity of the test compound were checked on the plants as sowed or planted. The results are shown in Table 3.

As to the application, a wettable powder preparation containing a required amount of the test compound was diluted with water and applied in a proportion of 15 ml/pot by means of a pipette. The herbicidal activity was evaluated according the same criteria as in Example I.

With regard to the evaluation of phytotoxicity, the three factors (i.e. height of plant, number of tillers and total weight (dry weight)) were each checked, and a ratio of the treated plot to the untreated plot was calculated for each factor. The phytotoxicity was evaluated based on the lowest value in the three factors, which was classified into the following grades ranging from 0 to 5.

| Grade | Ratio of the untreated plot (%) |
|---|---|
| 0 | 100 |
| 1 | 90–99 |
| 2 | 80–89 |
| 3 | 60–79 |
| 4 | 40–59 |
| 5 | 0–39 |

TABLE 3

| Compound No. | Dosage of active ingredient (g/are) | Herbicidal activity | | | Phytotoxicity |
|---|---|---|---|---|---|
| | | Pickerel weed | Scirpus Hotarui | Slender spikerush | Rice plant |
| 1 | 40 | 5 | 5 | 5 | 1 |
| | 20 | 5 | 5 | 5 | 0 |
| 2 | 40 | 5 | 5 | 5 | 1 |
| | 20 | 5 | 5 | 5 | 0 |
| 4 | 40 | 5 | 5 | 5 | 0 |
| | 20 | 5 | 5 | 5 | 0 |
| 6 | 40 | 5 | 5 | 5 | 0 |
| | 20 | 5 | 5 | 5 | 0 |
| 7 | 40 | 5 | 5 | 5 | 0 |
| | 20 | 4 | 5 | 5 | 0 |
| 9 | 40 | 4 | 5 | 5 | 0 |
| | 20 | 4 | 4 | 4 | 0 |
| 18 | 20 | 5 | 5 | 5 | 0 |
| | 10 | 5 | 5 | 5 | 0 |
| 33 | 20 | 5 | 5 | 5 | 0 |
| | 10 | 4 | 5 | 5 | 0 |
| 34 | 20 | 5 | 5 | 5 | 0 |
| | 10 | 5 | 5 | 5 | 0 |
| 38 | 20 | 5 | 5 | 5 | 0 |
| | 10 | 5 | 5 | 5 | 0 |
| 40 | 20 | 4 | 5 | 5 | 0 |
| | 10 | 1 | 5 | 5 | 0 |

EXAMPLE III

In a plastic pot (10 cm in diameter), upland soil was filled, and tubers of purple nutsedge (*Cyperus rotundus*) were transplanted at the depth of 2 cm from the soil surface and cultivated in a greenhouse for 4 weeks, whereby purple nutsedge was in 7-leaved stage. The required amount of the test compound each formulated into an emulsifiable concentrate preparation and diluted with water was applied to the foliage of the test plant by means of a hand sprayer and further grown in the greenhouse for 8 weeks, and then subjected to observation by removal of the soil with water. The herbicidal activity on the aerial part (e.g. leaves) and the underground part (e.g. rhizome and tuber) was evaluated according to the same criteria as in Example I. The results are shown in Table 4.

TABLE 4

| Compound No. | Dosage of active ingredient (g/are) | Herbicidal activity | |
| --- | --- | --- | --- |
| | | Aerial part | Underground part |
| 1 | 40 | 5 | 5 |
| | 20 | 5 | 5 |
| 2 | 40 | 5 | 5 |
| | 20 | 5 | 5 |
| 4 | 40 | 5 | 5 |
| | 20 | 4 | 5 |
| Control* | 40 | 5 | 5 |
| C | 20 | 4 | 5 |

Note:
Compound disclosed in U.S. Pat. No. 3,799,758 (known as "glyphosphate"); isopropylamine salt of a compound of the formula:

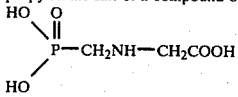

What is claimed is:
1. A compound of the formula:

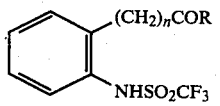

wherein R is $C_1$-$C_4$ alkylamino, $C_3$-$C_4$ alkenylamino, $C_3$-$C_4$ alkynylamino, di($C_1$-$C_4$)alkylamino, di($C_3$-$C_4$)alkenylamino, di($C_3$-$C_4$)alkynylamino, $C_1$-$C_4$ alkyl($C_3$-$C_4$)alkenylamino, $C_1$-$C_4$ alkyl($C_3$-$C_4$)alkynylamino, $C_1$-$C_4$ alkoxyamino, $C_1$-$C_4$ alkyl($C_1$-$C_4$)alkoxyamino, $C_1$-$C_4$ alkylphenylamino, morpholino, thiomorpholino, $C_1$-$C_4$ alkylmorpholino, di($C_1$-$C_4$)alkylmorpholino, pyrrolidino, $C_1$-$C_4$ alkylpyrrolidino, piperidino, $C_1$-$C_4$ alkylpiperidino, hexamethyleneimino or tetrahydropyridino and n is an integer of 0 or 1, or a salt thereof.

2. The compound according to claim 1, wherein R is $C_1$-$C_4$ alkylamino, $C_3$-$C_4$ alkenylamino, $C_3$-$C_4$ alkynylamino, di($C_1$-$C_4$)alkylamino, di($C_3$-$C_4$)alkenylamino, di($C_3$-$C_4$)-alkynylamino, $C_1$-$C_4$ alkyl($C_3$-$C_4$)alkenylamino or $C_1$-$C_4$ alkyl($C_3$-$C_4$)alkynylamino and n is an integer of 0.

3. The compound according to claim 1, wherein R is $C_1$-$C_4$ alkylamino, $C_3$-$C_4$ alkenylamino, $C_3$-$C_4$ alkynylamino, di($C_1$-$C_4$)alkylamino, di($C_3$-$C_4$)alkenylamino, di($C_3$-$C_4$)-alkynylamino, $C_1$-$C_4$ alkyl($C_3$-$C_4$)alkenylamino, $C_1$-$C_4$ alkyl($C_3$-$C_4$)alkynylamino, $C_1$-$C_4$ alkoxyamino, $C_1$-$C_4$ alkyl($C_1$-$C_4$)alkoxyamino, $C_1$-$C_4$ alkylphenylamino, morpholino, thiomorpholino, $C_1$-$C_4$ alkylmorpholino, di($C_1$-$C_4$)alkylmorpholino, pyrrolidino, $C_1$-$C_4$ alkylpyrrolidino, piperidino, $C_1$-$C_4$ alkylpiperidino, hexamethyleneimino or tetrahydropyridino and n is an integer of 1.

4. The compound according to claim 2, wherein R is $C_1$-$C_4$ alkylamino, allylamino, propargylamino or di($C_2$-$C_3$)alkylamino and n is an integer of 0.

5. The compound according to claim 3, wherein R is $C_1$-$C_2$ alkylamino, di($C_1$-$C_2$)alkylamino, diallylamino, dipropargylamino, methoxyamino, methoxymethylamino, $C_1$-$C_2$ alkylphenylamino, morpholino, thiomorpholino, pyrrolidino, piperidino, hexamethyleneimino, tetrahydropyridino, methylpiperidino or dimethylpyrrolidino and n is an integer of 1.

6. N-Ethyl-o-(trifluoromethanesulfonamido)-benzamide.

7. N-Methyl-o-(trifluoromethanesulfonamido)-benzamide.

8. N-Propargyl-o-(trifluoromethanesulfonamido)-benzamide.

9. N-Isopropyl-o-(trifluoromethanesulfonamido)-benzamide.

10. N-Methyl-N-n-propyl-O-(trifluoromethanesulfonamido)phenylacetamide.

11. N-[o-(Trifluoromethanesulfonamido)-phenylacetyl]-2,5-dimethylpyrrolidine.

12. N-[o-(Trifluoromethanesulfonamido)-phenylacetyl]hexamethyleneimine.

13. N-[o-(Trifluoromethanesulfonamido)-phenylacetyl]morpholine.

14. A herbicidal composition which comprises as an active ingredient a herbicidally effective amount of the compound according to claim 1 and an inert carrier or diluent.

15. A method for controlling weeds which comprises applying a herbicidally effective amount of the compound according to claim 1 to the area where the weeds grow or will grow.

16. The method according to claim 15, wherein the area is a farmland.

17. The method according to claim 16, wherein the farmland is a field where corn, wheat, cotton or soybean is cultivated or will be cultivated.

18. The method according to claim 15, wherein the area is a paddy field where rice plants are cultivated or will be cultivated.

* * * * *